United States Patent [19]

Ochiai

[11] Patent Number: 5,352,415
[45] Date of Patent: Oct. 4, 1994

[54] CONTROL SYSTEM FOR ACETIC ACID MANUFACTURING PROCESS

[75] Inventor: Shinya Ochiai, Corpus Christi, Tex.

[73] Assignee: Hoechst Celanese Corporation, Somerville, N.J.

[21] Appl. No.: 129,971

[22] Filed: Sep. 29, 1993

[51] Int. Cl.⁵ .................. G05D 9/00; G08B 21/00; B01J 8/00

[52] U.S. Cl. .................. 422/105; 422/106; 422/110; 422/234; 203/1; 562/519; 340/618

[58] Field of Search ............ 422/105, 106, 110, 234; 202/181; 203/1; 562/519; 367/908; 340/606, 611, 612, 614, 618, 626

[56]  References Cited

U.S. PATENT DOCUMENTS

| | | | |
|---|---|---|---|
| 3,769,329 | 10/1973 | Paulik et al. | 560/232 |
| 4,894,477 | 1/1990 | Scates et al. | 562/519 |
| 5,001,259 | 3/1991 | Smith et al. | 562/519 |
| 5,214,203 | 5/1993 | Koyama et al. | 562/519 |
| 5,252,295 | 10/1993 | Hovis et al. | 422/106 |

Primary Examiner—Timothy M. McMahon
Assistant Examiner—Christopher Y. Kim
Attorney, Agent, or Firm—Donald R. Cassady; Stuart D. Frenkel

[57]  ABSTRACT

A novel control system is provided to control the liquid levels in a reactor-flasher combination used particularly for the carbonylation of methanol to acetic acid. Liquid level control is achieved by proportional controllers or other controllers which do not continuously seek zero off-set from the desired level and which proportionally change the liquid flow rates from the respective reactor and flasher. An adjustment can be made to the level controllers to change the liquid flow rates by a function generator which adjusts the flow rate, according to an empirically derived function which correlates changes in methanol feed rate to liquid flow rates from the reactor and flasher.

18 Claims, 6 Drawing Sheets

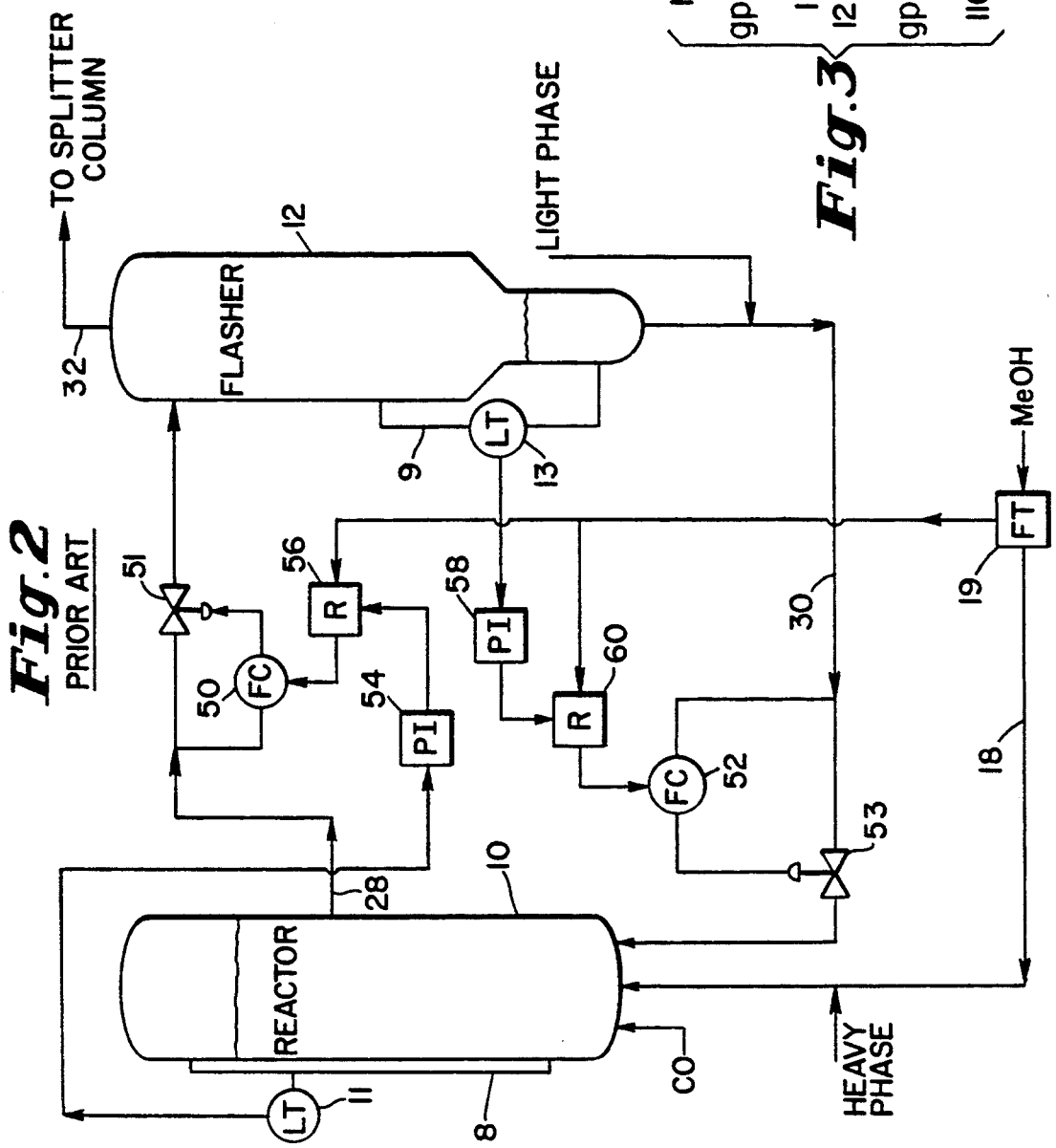

CONTROL SYSTEM FOR ACETIC ACID MANUFACTURING PROCESS

FIELD OF THE INVENTION

The present invention is concerned with an improved control system for reducing the variability of reactor product and catalyst recycle flow rate as well as reactor and flasher liquid levels in a process for the rhodium-catalyzed carbonylation of methanol to acetic acid.

BACKGROUND OF THE INVENTION

Among currently employed processes for synthesizing acetic acid, one of the most useful commercially is the catalyzed carbonylation of methanol with carbon monoxide as set forth in U.S. Pat. No. 3,769,329, issued Oct. 30, 1973. The carbonylation catalyst comprises rhodium along with a catalyst promoter exemplified by methyl iodide. The reaction is conducted with the catalyst being dissolved in a liquid reaction medium through which carbon monoxide gas is continuously bubbled. The rhodium-catalyzed carbonylation of methanol to acetic acid as described in this patent is very selective to the acetic acid product and as such offers substantial advantages over oxidation processes in which multiple distillations are required to separate the acid product from the other oxygenated products which are formed.

An improvement in the rhodium-catalyzed carbonylation of methanol to acetic acid is set forth in commonly assigned U.S. Pat. Nos. 5,001,259; 5,026,908 and 5,144,068. As disclosed therein, acetic acid is produced by the carbonylation of methanol in a reaction medium comprised of methyl acetate, methyl iodide, rhodium and an additional iodide salt such as lithium iodide and wherein the water concentration in the reactor is maintained at below 14 weight percent. This process has been characterized as the "low water" carbonylation process as distinguished from prior commercial adaptation of the teachings in U.S. Pat. No. 3,769,328 wherein greater than 14 wt. % water was maintained in the reaction medium and which prior process has been characterized as the "high water" carbonylation process. It has been found that catalyst stability and the productivity of the carbonylation reactor can be maintained at surprisingly high levels even at the low water concentration of below 14 weight percent and even at very low water concentrations of 4 weight percent or less. The high reaction rates and improved productivity are quite surprising in view of the prior art which disclosed the benefits of high water to improve reaction rates and in view of the high propensity of the rhodium to precipitate from the solution especially at water levels of below 14 weight percent. By utilizing less water in the reaction medium, downstream purification to remove water from the acetic acid product is substantially reduced. Accordingly, by providing increased productivity in the reactor, the overall productivity of the low water carbonylation process is vastly improved over productivity in the high water process.

The reaction system which is employed in the rhodium-catalyzed carbonylation of methanol to acetic acid comprises a liquid-phase carbonylation reactor, a flasher for catalyst recycle, a methyl iodide-acetic acid splitter column and a drying column. The carbonylation reactor is typically a stirred autoclave within which the reacting liquid contents are maintained automatically at a constant level. Into the reactor there are continuously introduced fresh methanol, sufficient water, recycled catalyst solution from the flasher base and recycled methyl iodide, methyl acetate and water from distillation. The reactor product is discharged to the flasher wherein a liquid catalyst solution is withdrawn as a base stream containing predominately rhodium and acetic acid as well as the iodide salt along with lesser quantities of methyl acetate, methyl iodide and water while the overhead of the flasher is a vapor comprising largely the acetic acid product along with methyl iodide, methyl acetate and water. The catalyst solution withdrawn from the flasher base is recycled to the reactor. The flasher vapor is then fed to the distillation unit wherein the product acetic acid is typically withdrawn from the middle of the splitter column and then directed to the drying column for removal of water. The overhead from the splitter column contains a heavy phase of aqueous methyl iodide and methyl acetate and a light phase comprising aqueous acetic acid. The water removed from acetic acid product in the drying stage contains small amounts of acetic acid and can be combined with the light aqueous acetic acid phase from the splitter column. The heavy phase, light phase and water from the distillations are returned to the reactor.

Implementation of the low water carbonylation process necessitated changes in the means to control the liquid levels in the reactor and flasher that were used under high water carbonylation conditions. Unfortunately, such changes have led to a wider variability in these liquid levels as well as reactor product flow rate and flasher recycle flow rate per a given methanol feed rate to the reactor. While a steady state of dry acetic acid product has been maintained from the distillation system per methanol feed rate, process inefficiency in the form of variable liquid levels and flow rates of the intermediate process streams is economically disadvantageous.

Prior to the introduction of the low water operating conditions, the exothermic heat of reaction could be absorbed by the solvent medium including water and removed almost solely by the reactor product flow to the flasher. Thus, to control temperature in the reactor there was established a fixed relationship between the methanol feed rate and the reactor product flow rate to the flasher. This fixed relationship led to narrow variability in the liquid level in the reactor and intermediate process streams. However, upon implementation of the low water technology as described in the aforementioned commonly assigned U.S. Pat. No. 5,001,259, the amount of water in the reactor was reduced and, as a consequence of the reduced heat sink, the reactor and the catalyst recycle flow from the flasher base were provided with coolers to remove the heat of reaction in addition to heat removal via the product flow to the flasher. With the addition of the cooling means, the fixed relationship between the methanol feed rate and the product flow rate from the reactor to the flasher in order to control temperature no longer existed. Accordingly, the use of the coolers and the consequent loss of the fixed relationship between methanol feed and the manipulated reactor product flow rate to the flasher resulted in a wider variability of the reactor and flasher liquid levels as well as the reactor product and catalyst recycle flow rates even under a constant methanol feed rate to the reactor.

Prior to the present invention, liquid level control in the reactor and flasher was achieved by level controllers with both proportional and integral control elements. The level controllers affected changes in reactor product and catalyst recycle flow rates in response to deviations in the liquid levels so as to maintain the desired set liquid levels in the respective vessels. The loss of the fixed relationship between methanol feed rate and product flow rate to the flasher as described above resulted in a greater reliance on the integral controller to maintain the proper liquid levels and flow rates. The integral control mode, however, continuously seeks to achieve zero off-set from the set point of the controller and, accordingly, substantial oscillation occurred in the affected variables during the corrections by the controller. In particular, substantial variation occurred in the reactor level and reactor product flow rate, flasher level and catalyst recycle from the flasher to the reactor as well as recycle flow rates from the distillation apparatus including the splitter column and drying column as the integral controller attempted to achieve zero off-set from the set liquid levels in the respective vessels. Importantly, in addition to changes made in the reactor product flow rate and catalyst recycle flow rate in response to deviations of the liquid levels from the level set points of the reactor and flasher, changes in the respective flow rates were also made proportional to changes in the methanol feed rate by employment of a multiplier which commanded the set point for the flow controllers. In fact, a major reason for liquid level deviations from the set point was due to changes in the methanol feed rate to the reactor. Unfortunately, the proportional changes made in the reactor product flow rate and catalyst recycle flow rate relative to the changes in methanol feed rate did not accurately represent the changes empirically taking place during the carbonylation reaction inasmuch as the reactor product flow rate and catalyst recycle flow rate do not change proportionally to changes in the methanol feed rate at steady state.

A proportional only control would be insufficient to correct the deviations of the liquid level as a substantial off-set from the set point of the controllers would likely still remain if coupled with the inaccurate multiplier to adjust for changes in the methanol feed rate. The integral controller while correcting the liquid level off-set causes substantial oscillations in the process variables during the operation thereof as described above. The wide variability in liquid levels and flow rates of the intermediate process streams as a result of the integral controller and inaccurate multiplier leads to process inefficiencies. The inefficiencies are manifested in excessive liquid being treated in the distillation train, excessive steam requirements for distillation, poor product quality and eventually lower methanol feed rates to reduce purification needs and consequent reduction in productivity.

Accordingly, there is a need to reduce the variability of the liquid levels in the reactor and flasher as well as the reactor product flow rate to the flasher and catalyst recycle flow rate from the base of the flasher to the reactor relative to both a constant and changing methanol feed rate to the reactor. The objects of the present invention address such need. Thus, the objective of the present invention is primarily directed to improve the operation of a reactor-flasher combination used in the rhodium-catalyzed carbonylation of methanol to acetic acid but can be directed to reduce operational variability in any reaction using the reactor-flasher combination.

SUMMARY OF THE INVENTION

In the process for carbonylating a methanol feed to acetic acid utilizing a reactor and flasher combination, it has been found important to reduce the variability of liquid levels in the reactor and flasher as well as reduce variability of the flow rates of the intermediate streams relative to the methanol feed rate so as to improve process efficiency. In accordance with the present invention, the integral plus proportional level controllers for the reactor and flasher used in the prior art process are replaced with controllers which do not endlessly seek a zero off-set from the set point, e.g. proportional only controller or controller with a lead-lag element. Thus, oscillations in process variables are reduced by eliminating the integral control mode. The use of such level controllers, however, requires an additional means to make the necessary adjustment to flow rates based on a more accurate representation of the changes in product flow rate and catalyst recycle flow rate taking place relative to the changes in methanol feed rate than has previously been used inasmuch as changes in the methanol feed rate are the primary reason for liquid level off-sets in the reactor and flasher vessels. Accordingly, reactor product flow rate and catalyst recycle flow rate from the flasher are also adjusted by input from a function generator which correlates changes in the methanol feed rate to desired changes in the reactor product and catalyst recycle flow rates by means of a function empirically-derived from steady state process conditions. The function generator replaces the inaccurate multiplier. Control of the flow rates of the reactor product and catalyst recycle is now achieved by the summation of inputs from the respective level controllers and the function generator.

The elimination of the integral controller and the more accurate representation of reaction conditions by means of the function generator reduces the oscillations of the liquid levels and flow rates of the intermediate process streams as the control scheme operates to maintain set liquid levels. This improves the process efficiency.

BRIEF DESCRIPTION OF THE DRAWINGS

FIG. 2 is schematic diagram showing the level control scheme for the reactor and flasher which has previously been used in the process for carbonylating methanol to acetic acid.

FIG. 3 is a pair of graphs illustrating the side by side comparison of methanol feed rate and the actual reactor product flow rate to the flasher which results utilizing the control scheme of FIG. 2.

DETAILED DESCRIPTION OF THE INVENTION

The process of the present invention is particularly useful in the carbonylation of methanol to acetic acid as practiced in which the carbonylation reaction takes place in the liquid phase in a reactor and in which the acetic acid product from the reactor is directed to a flasher which vaporizes the product and directs same to a distillation system and wherein the liquid catalyst which remains in the flasher is recycled to the reactor. Besides the methanol carbonylation to acetic acid, the invention may also be useful in controlling product and recycle flows in any reaction system utilizing a reactor-flasher combination.

In particular, however, the invention is most useful in the carbonylation of methanol to acetic acid and especially when such carbonylation takes place under the low water conditions as exemplified in U.S. Pat. No. 5,001,259, mentioned above. In the carbonylation process, the catalyst which is employed includes a rhodium component and a halogen promoter in which the halogen is either bromine or iodine. Preferably, the halogen compound is an organic halide and, more specifically, is methyl iodide. The liquid reaction medium which is employed includes any solvent compatible with the catalyst system and, most preferably, comprises the carboxylic acid product. Thus, in the carbonylation of methanol to acetic acid, the preferred solvent is acetic acid. Water is also included in the reaction medium but under the "low water" conditions is present at concentrations below 14 wt. %. Preferably, the carbonylation takes place at a water concentration in the reaction medium of less than 10 wt. % and, most preferably, at water concentrations of from finite levels as a minimum up to 4 wt. %. The level control system of this invention is also useful for "high water" carbonylation conditions which typically operate at water concentrations of above 14 wt. % to about 15 wt. %.

Even under the low water operating conditions, the desired reaction rates are obtained by including in the reaction medium an ester which corresponds to the alcohol being carbonylated and the acid product of the carbonylation reaction and an additional iodide ion which is over and above the iodide which is present as the catalyst promoter. Thus, in the carbonylation of methanol to acetic acid, the ester is methyl acetate and the additional iodide promoter is an iodide salt, preferably lithium iodide. Typical reaction temperatures for carbonylation will be approximately 150°-250° C., with the temperature range of about 180°-220° C. being the preferred range. The carbon monoxide partial pressure in the reactor can vary widely and is typically about 2 to 30 atmospheres, and, preferably, about 4 to 15 atmospheres. The reaction medium and operating conditions are adequately described in aforementioned U.S. Pat. No. 5,001,259, the contents of which are herein incorporated by reference.

Figure 1:
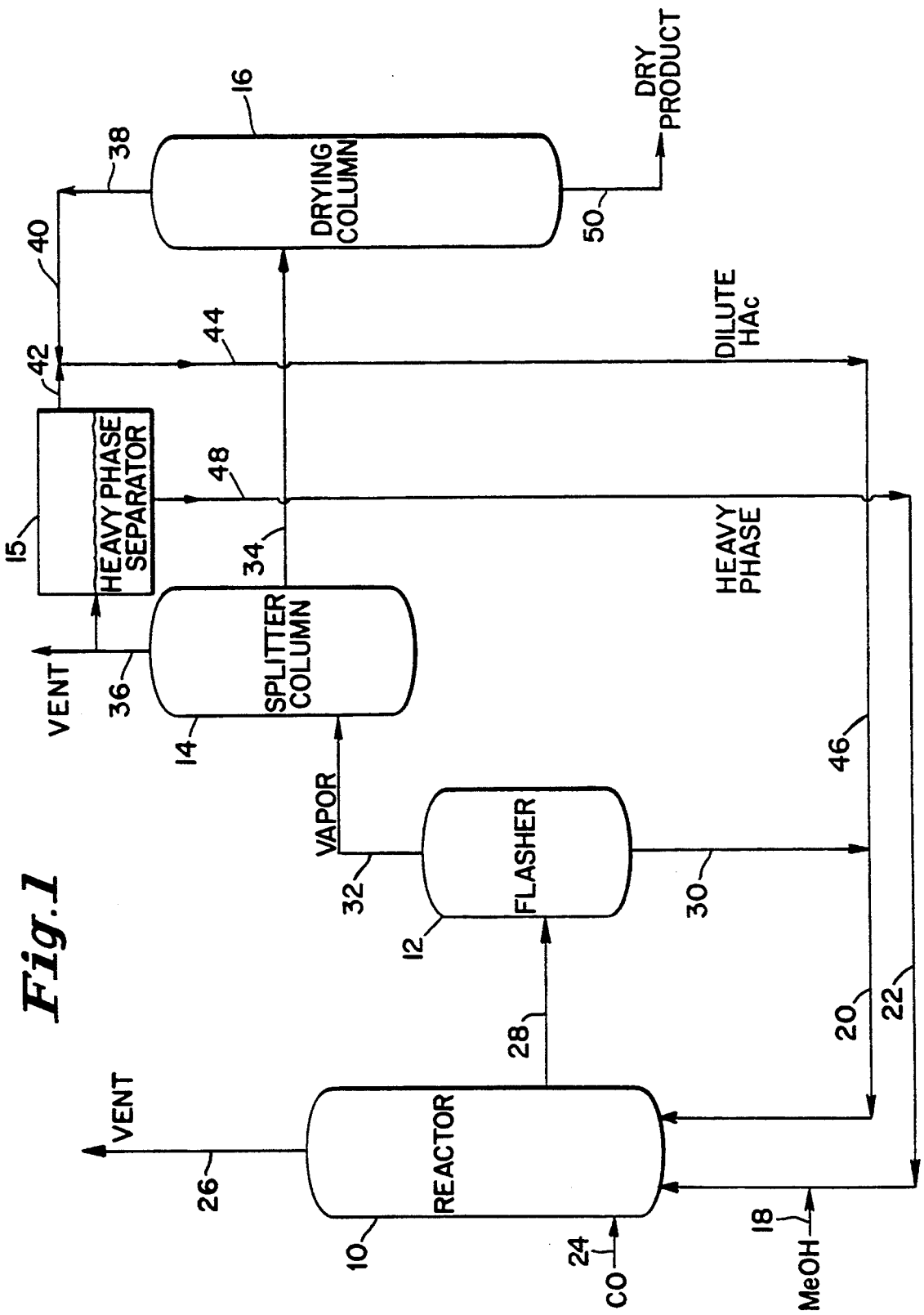
FIG. 1 is a schematic illustration showing the carbonylation process of the present invention in which the process flows between the reactor, flasher and distillation system are set forth.

The reaction system which is employed in the carbonylation of methanol to acetic acid is illustrated in FIG. 1 and comprises a liquid-phase carbonylation reactor 10, a flasher 12, and a distillation system comprising a methyl iodide-acetic acid splitter column 14, a heavy phase separator 15 and a drying column 16. The carbonylation reactor 10 is typically a stirred autoclave within which the reacting liquid contents are maintained at a constant level. Into this reactor, there are continuously introduced fresh methanol from line 18, recycled catalyst solution directed from the flasher base via line 20 and recycled methyl iodide, methyl acetate, acetic acid and water via lines 22 and 46 from the overhead of splitter column 14 and drying column 16. The carbon monoxide feed via line 24 is continuously introduced into carbonylation reactor 10 just below the agitator which is used to stir the contents. The gaseous feed is, of course, thoroughly dispersed throughout the reactive liquid by this means. A gaseous purge stream 26 is vented from reactor 10 to prevent buildup of gaseous byproducts and to maintain a set carbon monoxide partial pressure at a given total reactor pressure.

The liquid product is drawn off from carbonylation reactor 10 via line 28 at a rate sufficient to maintain a constant level therein and is introduced to flasher 12 at a point intermediate between the top and bottom thereof. In flasher 12, the catalyst solution is withdrawn as a base stream 30 (predominantly acetic acid containing rhodium and the iodide salt along with lesser quantities of methyl acetate, methyl iodide and water), while the overhead 32 of flasher 12 comprises largely the product acetic acid along with methyl iodide, methyl acetate, and water.

The product acetic acid is withdrawn from the base of the splitter column 14 or as a side stream 34 as shown in FIG. 1 and is directed to the final purification such as drying column 16. The overhead 36 from splitter column 14 contains a heavy phase of aqueous methyl iodide and methyl acetate and a light phase comprising aqueous acetic acid. The separate phases are divided in heavy phase separator 15 to yield a heavy phase stream 48 and a light phase stream 42. Water separated from product acetic acid in drying column 16 will contain small amounts of acetic acid and can be withdrawn from overhead drying column 16 via line 38 and combined via line 40 with the light phase leaving separator 15 via line 42 and returned to the reactor via lines 44, 46 and 20. The heavy phase via line 48 can also be recycled to the reactor via line 22 to reduce the amount of fresh methyl iodide and methyl acetate needed to be fed to reactor 10. More specifically, the light phase taken from overhead splitter column 14 and the dilute acetic acid taken from overhead drying column 16 are combined with the recycled catalyst from flasher 12 while the heavy phase taken from overhead splitter column 14 is combined with the methanol feed to the reactor as shown. Dry product acetic acid is withdrawn from the base of drying column 16 via line 50.

The liquid levels in reactor 10 and flasher 12 are automatically controlled as is the temperature in these vessels. Temperature control in the reactor is necessary inasmuch as the carbonylation reaction is exothermic. To maintain the desired temperature previous to this invention, there was maintained a direct relationship between the amount of product removed from the reactor via line 28 so as to remove heat therefrom and the amount of fresh methanol feed which was added to reactor 10 via line 18. Unfortunately, by removing the heat from the reactor by withdrawing a substantial amount of product, a large amount of recycle had to be returned to the reactor 10 at steady state conditions. This recycle of product to the reactor was inefficient.

In order to reduce the dependence of temperature control in the reactor primarily on the flow rate of the reactor product directed to the flasher, coolers have been placed on the reactor as well as the catalyst recycle flow from the flasher base. The addition of the coolers has allowed reduction in the reactor product flow rate and consequent reduction in the amount of recycle to the reactor for a given methanol feed rate. Thus, with the addition of the reactor cooler and catalyst recycle cooler the ratio of the reactor product flow rate to methanol feed rate is typically below 7.0 whereas prior to use of the coolers and wherein temperature control was achieved previously by removing the product from the reactor the ratio of reactor product flow rate to methanol feed rate was about 11.0 and above. Reduction in reaction product flow rate to the flasher reduced the amount of non-acid product vapor produced in flasher 12 and consequently reduced the downstream distillation requirements to purify the acid product.

Unfortunately, with the addition of the coolers, the fixed relationship between the methanol feed rate and the reactor product feed rate so as to control temperature was eliminated. Similarly, the use of the coolers contributed to reduce the flow rate of the light phase recycle flow from overhead the drying column 16 via lines 40 and 42 to the reactor 10. The light phase flow to the reactor which was a manipulated variable for reactor level control became too small to control the reactor level. Therefore, the use of the coolers and the consequent loss of the light phase recycle as a manipulative variable resulted in a wider variability in the liquid levels in the reactor and flasher and as well in the reactor product and catalyst recycle flow rates even under a constant methanol feed rate.

With the addition of the reactor cooler and the catalyst recycle cooler, an alternative level control system for the reactor and flasher and flow control for reactor product and catalyst recycle flows has been used. This prior art control system is set forth in FIG. 2. Referring to FIG. 2, it can be seen that the liquid levels of reactor 10 and flasher 12 are dependent on the flow rates of the reactor product and catalyst recycle to and from the respective vessels. At the same time, the flow rate of the reactor product via line 28 to the flasher and the flow rate of catalyst recycle via line 30 to reactor 10 are dependent on the level control for each of the respective reactor and flasher vessels and the methanol feed rate to the reactor via line 18. This interdependence between liquid level and flow-rate control in the reactor-flasher combination is illustrated in FIG. 2. Thus, level control in reactor 10 and flasher 12, is achieved by altering the flow rate of reactor product and catalyst recycle from the respective vessels. Likewise, flow rate control is affected by input of actual liquid levels in the reactor 10 and flasher 12. In the prior art control scheme as shown in FIG. 2, actual liquid levels in reactor 10 and flasher 12 were determined by any known type of instrumentation, such as devices to measure differential pressure between the top vapor portion and lower liquid portion of the vessel or nuclear measurements, etc. Differential pressure measurement in columns 8 and 9 for reactor 10 and flasher 12, respectively, are depicted in FIG. 2. Referring to the prior art level control in reactor 10, the measurement of the actual liquid level therein was determined and directed via level transmitter 11 to level controller 54 which was a controller containing both proportional and integral elements. The actual level output from level transmitter 11 was received by controller 54 and compared to the set point for reactor level control. The difference or off-set between the set point for the liquid level and the actual liquid level in the reactor was corrected by controller 54 which generated a correctional signal. Multiplier 56 multiplied the correction signal from controller 54 with the rate of methanol feed passing through line 18 and determined and transmitted by flow transmitter 19 to provide a command signal to flow controller 50 which adjusted the flow rate of reactor product through valve 51 to the desired volume to correct the liquid level in reactor 10. The integral element of controller 54 inasmuch as it sought zero off-set from the liquid level set point for reactor 10 caused substantial oscillation in the flow rate and level during the control operation.

Level control in flasher 12 was provided by the same scheme as in place for reactor 10. Again referring to FIG. 2, the actual liquid level in flasher 12 was determined and directed via level transmitter 13 to level controller 58 which was also a proportional plus integral controller. The actual level output from level transmitter 13 was received by controller 58 and compared to the set point for the flasher liquid level. The off-set from the set point of the liquid level in the flasher was corrected by controller 58 which generated a correction signal. Multiplier 60 multiplied the correction signal from controller 54 and the methanol feed rate through line 18 determined and transmitted by flow transmitter 19 to provide a command signal for flow controller 52 which adjusted the flow rate of the catalyst recycle from flasher 12 via line 30 through valve 53 to correct the liquid level in flasher 12. Again, since the integral element of controller 58 endlessly sought a zero off-set from the level set point, oscillations in the flow rate and liquid level occurred during the control operation.

The oscillations of liquid levels and flow rates as discussed above was exacerbated due to the reactor-flasher combination and the interdependence between the respective liquid levels in each vessel as well as the interdependence between the liquid levels and flow rates to and from the reactor and flasher vessels. The variability at least with respect to the reactor product flow rate from reactor 10 via line 28 can be seen in FIG. 3 which represents data from the carbonylation system depicted in FIG. 1 and in which the level control scheme of FIG. 2 was in operation. Thus, it can be seen that over a forty hour period, the methanol feed rate was relatively constant except for an abrupt change at hour 30. However, the reactor product flow rate varied considerably over the 40 hour period.

Additional difficulty occurred during changes in methanol feed rate. Such changes were the major reason there occurred deviation from the level set points in the reactor and flasher vessels. Unfortunately, the proportional changes in reactor product and catalyst recycle flow rates directed by multipliers 56 and 60 did not accurately reflect the changes in actual reactor product and catalyst recycle flow rates taking place in response to the methanol feed rate changes during steady state operation. Due to the inaccurate command from multipliers 56 and 60, off-sets from the liquid level set points in the respective reactor and flasher vessels readily occurred. While the integral controller eventually corrected for this error, the correcting action caused oscillation of the liquid levels in the reactor and flasher as well as the flow rates as described previously. Thus, the proportional plus integral controllers 54 and 58 and the multiplier controls 56 and 60 contributed to the wide variability in the flow rates and liquid levels.

Figure 4:
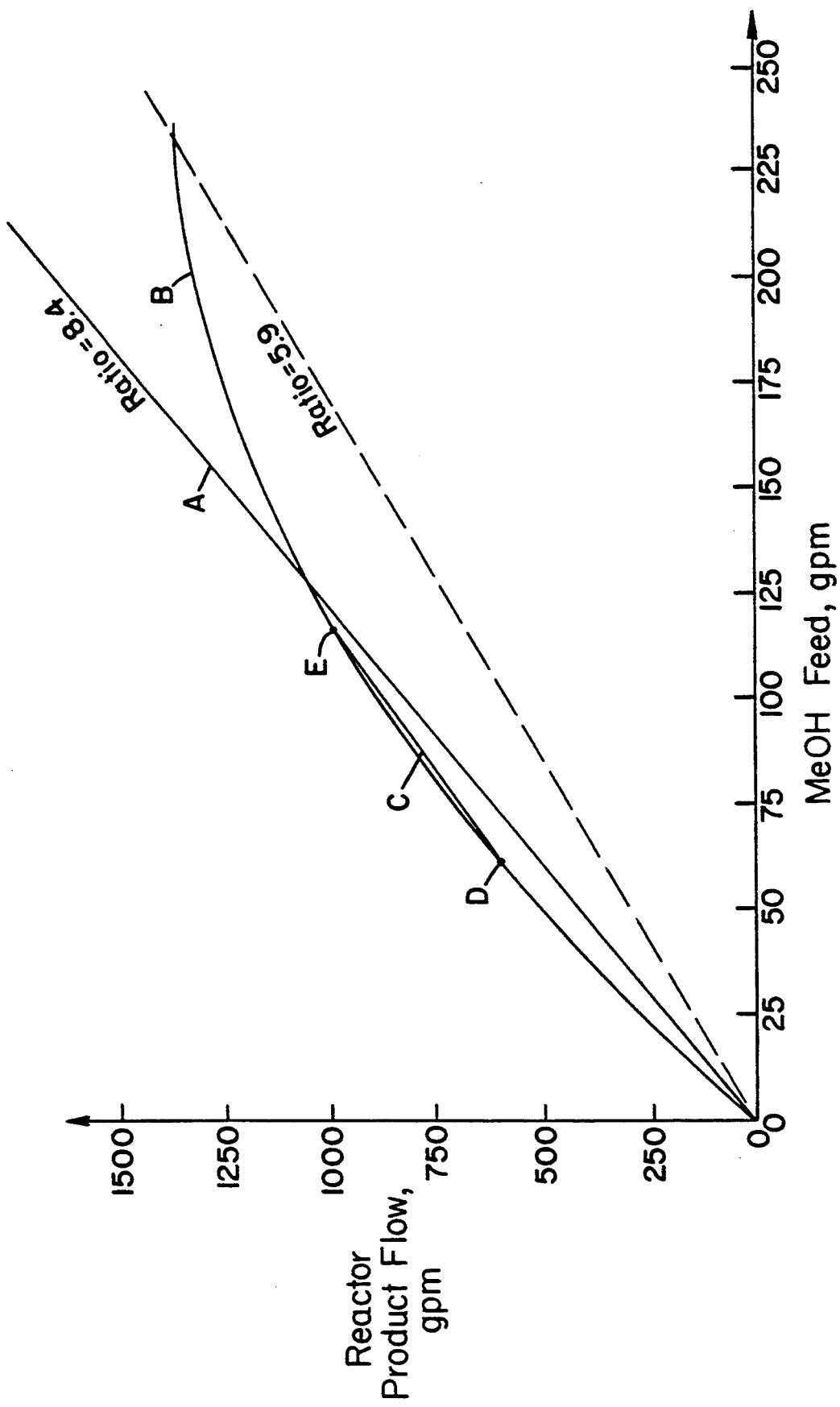
FIG. 4 is a graph of empirical data which has been generated from the carbonylation of methanol to acetic acid showing the relationship between the methanol feed rate to the reactor and the reactor product flow rate from the reactor to the flasher.
Figure 5:
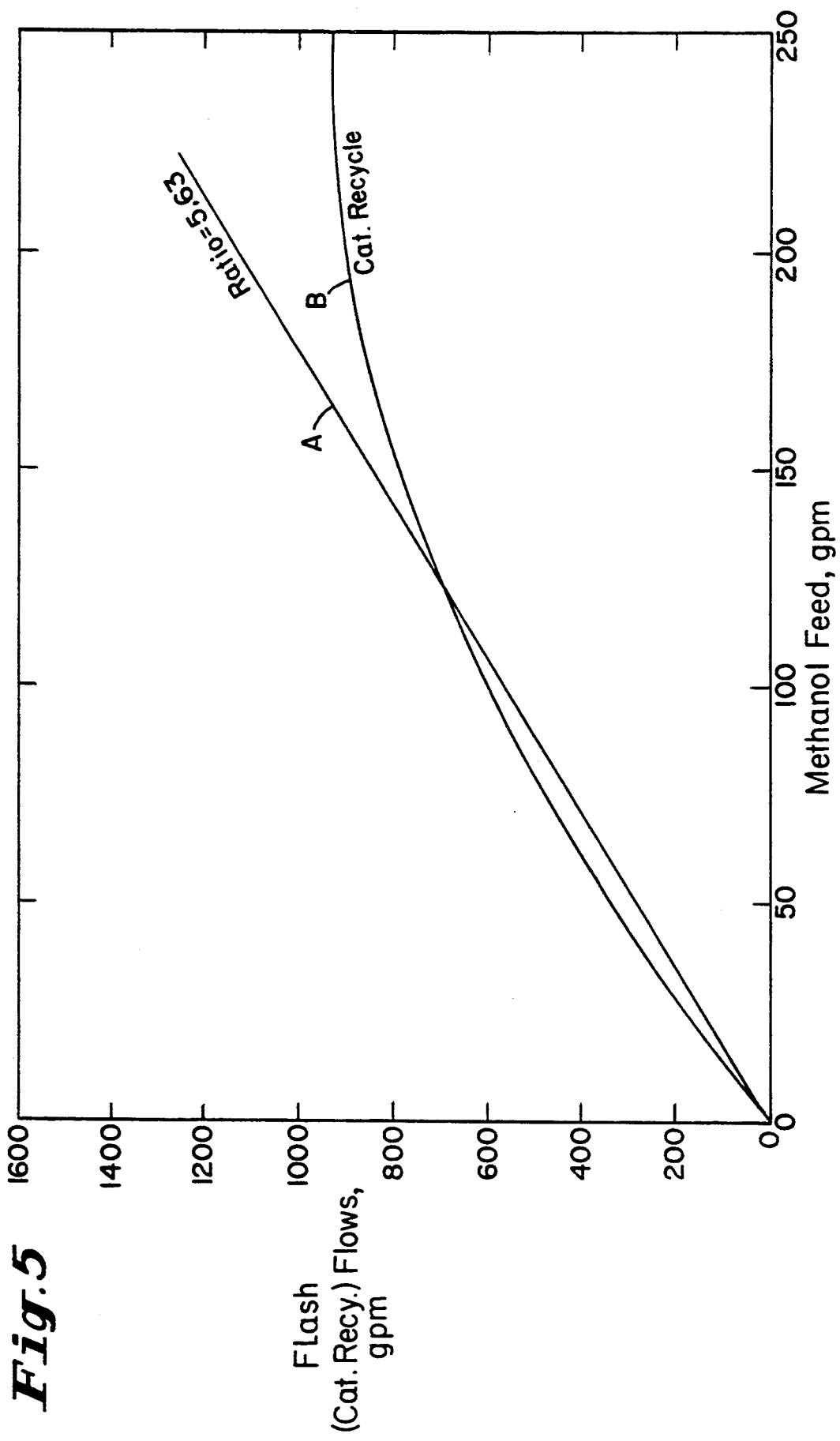
FIG. 5 is a graph of empirical data generated from the carbonylation of methanol to acetic acid showing the relationship between the methanol feed rate and the flow rate of the catalyst recycle from the flasher to the reactor.

The error in the proportional changes commanded by multipliers 56 and 60 is shown in FIGS. 4 and 5. As shown in FIG. 4, curve A represents the relationship between reactor product flow rate and methanol feed rate as commanded by multiplier 56 to set flow controller 50 wherein the ratio of the reactor product flow rate to methanol feed rate in gallons per minute is 8.4. Under steady state conditions, however, the actual ratio of the reactor product flow rate and methanol feed rate does not follow the proportional change commanded by multiplier 56. The actual relationship between product reactor flow rate and methanol feed rate at steady state conditions is represented by curve B wherein the ratio of reactor product flow rate to methanol feed rate gradually decreases as the methanol feed rate increases. FIG. 5 illustrates the relationship between catalyst recycle flow rate from flasher 12 and methanol feed rate wherein curve A represents such relationship as commanded by output from the multiplier 60 whereas curve B represents the actual relationship between the two streams which exist during steady state operation of the carbonylation reaction. The integral control mode eventually corrected the liquid level off-set invariably resulting from the error of the multiplier, but as previously discussed this control mode caused substantial oscillation during the correction cycle. Correction of the level off-set caused by the inaccurate representation of actual reaction conditions by the multiplier cannot readily be achieved by proportional control only as a substantial off-set would likely remain even though flow rates would be more stable.

Figure 6:
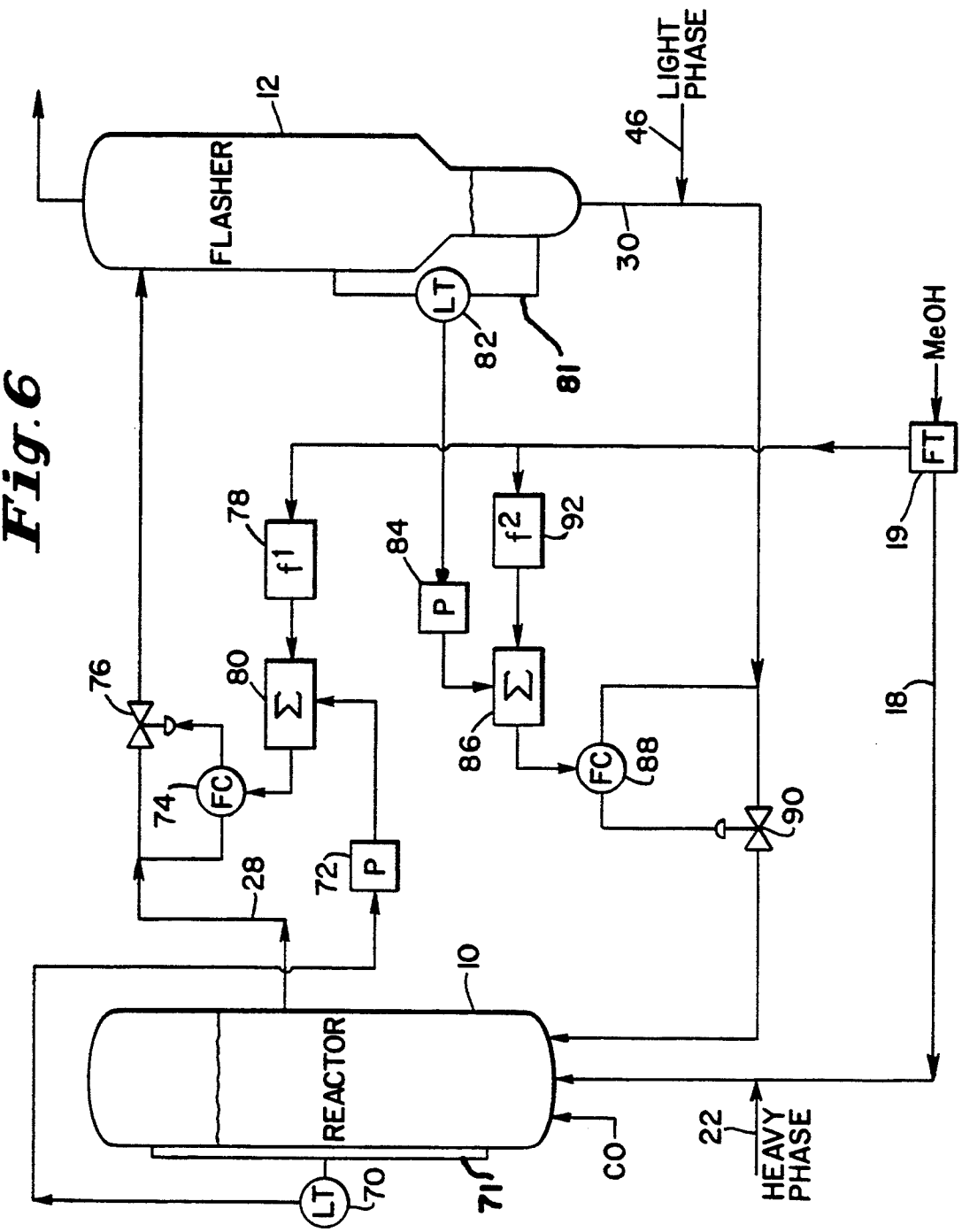
FIG. 6 is a schematic diagram of the level control system of the present invention.

The control system of the present invention as depicted in FIG. 6 eliminates the integral control mode of the prior art. To reduce off-sets from the set liquid levels as a result of proportional only control, and in particular, caused by changes in the methanol feed rate, the prior art multipliers are replaced with function generators each of which transmit a signal which represents the actual relationship between methanol feed rate and the respective feed rates of the reactor product and catalyst recycle which exists during steady state operation of the carbonylation reaction. Thus, the function generators provide a signal to adjust the respective reactor product and catalyst recycle flow rates with respect to changes in methanol feed rate along represented curves B as shown in FIGS. 4 and 5.

Referring now to FIG. 6, the control system of the present invention still must contend with the interdependence of liquid levels in the reactor and flasher and flow rates of the reactor product, catalyst recycle and methanol feed as in the control system of the prior art. However, in the control system of the present invention the integral control elements are eliminated and replaced with controllers which do not endlessly correct any off-set regardless of how minimal and, thus, do not seek zero liquid level off-set. Accordingly, level control is achieved by proportional only control or control with a lead-lag element. In the control system of the present invention, liquid level transmitter 70, which determines the actual reactor level such as by differential pressure in column 71, provides the input for proportional controller 72. Controller 72 corrects for any difference which exists between the set point for the liquid level in the reactor and the present level as signalled by level transmitter 70 by signalling a proportional change in reactor product flow rate. This correction signal is input to command flow controller 74 via summer 80 to set the volume flow of reactor product from reactor 10 via line 28 through valve 76 to the flasher 12. The command signal for flow controller 74 is actually determined by the summation of the input received from proportional controller 72 and a bias adjustment which is the input received from function generator 78. Even though a slight off-set from the level control set point may result by use of the proportional only control, such off-set is acceptable because the proportional only control will not seek a zero off-set if the reactor level remains constant and, thus, yields more stability to the liquid level and reactor product flow rate and, consequently, avoids the substantial oscillations inherent during integral control.

The control of the liquid level in flasher 12 and the flow rate of the catalyst recycle from flasher 12 via line 30 is essentially identical with the control of the reactor liquid level and reactor product withdrawn from reactor 10 and directed to flasher 12 via line 28. Thus, level transmitter 82 determines the actual liquid level in flasher 12 by differential pressure in column 81 and provides the measurement as an input for proportional controller 84. Controller 84 corrects the difference between the set point for the liquid level in the flasher and the present level signalled by level transmitter 82 by signalling a proportional change in catalyst recycle flow rate. This correction signal is fed to summer 86 to adjust the set point for flow controller 88 which controls the volume of catalyst recycle flow through valve 90.

The proportional only control for liquid levels in the reactor 10 and flasher 12 is enhanced by an adjustment bias from the respective function generators 78 and 92 which can accurately determine the adjustments to be made in reactor product and catalyst recycle flow rates in response to changes in methanol feed rate. The output of the function generators vary relative to the changes in the methanol feed rate entering the reactor 10 via line 18 and transmitted by flow transmitter 19. Function generator 78 as opposed to the multiplier of the prior art which did not accurately depict actual operating conditions instead correlates changes in the methanol feed rate via line 18 to changes in reactor product flow rate via line 28 by means of empirically derived function ($f^1$) which is represented by curve B as set forth in FIG. 4. Function generator 78 may also provide the adjustment bias by using a close approximation of the empirical relationship between reactor product flow rate and methanol feed rate by correlating the respective flow rates along one or more linear chords passing between two points on curve B and thereby simplify function $f^1$. An example would be chord C which passes between points D and E on cure B as shown in FIG. 4. Summer 80 adds the correction signal from proportional controller 72 and the bias signal from function generator 78 to provide the command signal for flow controller 74. Flow controller 74 sets valve 76 to the desired reactor product flow rate to achieve the proper level in reactor 10.

Likewise, to set the desired catalyst recycle flow via line 30 from flasher 12, a command signal is generated by summer 86 and directed to flow controller 88. The command signal is the sum of the correction signal from proportional controller 84 and the bias signal from function generator 92 which adjusts via function f² the catalyst recycle flow rate in response to changes in methanol feed rate through line 18. Function f² has been empirically derived and represents the actual relationship which exists between the methanol feed rate and catalyst recycle flow rate at steady state conditions and is depicted by curve B in FIG. 5. Again, to simplify the control function f², curve B can be divided into a series of linear chords which approximate curve B. The simplified function can be used by function generator 92. Summer 86 adds the input received from proportional controller 84 and the bias signal from function generator 92 to command the flow controller 88 to set the desired flow of catalyst recycle through valve 90 to maintain the desired liquid level in flasher 12. Again, the proportional only control 84 is acceptable and provides sufficient correction to minimize the off-set in flasher liquid level because of the accurate adjustment provided by the function generator 92 relative to changes in methanol feed rate, which changes cause the major deviation from the liquid level set point.

Without the integral control which continuously corrected for even minimal differences in the actual liquid levels of the reactor and flasher from the set point of the levels and which caused substantial oscillations of the liquid levels and flow rates as the controller sought zero off-set, the control system of the present invention eliminates such oscillations and importantly, substitutes the multipliers of the prior art with function generators which depict actual operating conditions at steady state to adjust the reactor product and catalyst recycle flow rates accurately with respect to changes in methanol feed rate. As changes in the methanol feed rate cause the greatest deviation from the level set point, only minimal off-sets if any are formed due to the proportion only level control.

The operating conditions for the carbonylation reaction with the control system of the present invention in place, are no different than as previously described. In fact, it is not contemplated that any changes in any reaction utilizing the reactor-flasher combination would have to be modified to accommodate the present control scheme.

In the carbonylation of methanol to acetic acid, with the control system of the present invention as depicted in FIG. 6 in operation, it is preferred to maintain the ratio of the reactor product flow rate to methanol feed rate in gallons per minute at between 5.0 to 8.0, most preferably between about 5.8 to 7.0. Preferably, the reactor and flasher proportional level controllers 72 and 84 will produce a gain of about 2% of the reactor product or catalyst recycle flow span per each percent of change in the reactor level span which equates to a proportional band of 50%. Different gains may be useful in the carbonylation process and any other process which utilizes the reactor-flasher combination without departing from the scope of the present invention. The change in the reactor product flow and catalyst recycle flow volume provided by the gain in volume flow signalled by the proportional controllers is also biased by the addition of volume flow signaled by the function generator. A zero change in the methanol feed rate would mean that the function generator would not add an adjustment bias to the adjustment already commanded by the respective proportional controllers.

The useful proportional controllers or controllers with a lead-lag element as described previously are such as to not endlessly seek a zero off-set from the set point of the level controllers. What is meant by this is that the proportional controllers once a constant liquid level has been maintained cannot adjust the flow rates even though an off-set may still remain. This is in contrast to the integral control mode which sought a zero off-set regardless of the stability of the liquid levels in the respective reactor and flasher vessels.

The control system of the present invention is particularly useful in the rhodium-catalyzed carbonylation of methanol to acetic acid under the low water conditions previously explained. In addition, it is believed that the control system is also useful in any reaction system which relies upon a liquid phase reactor and a flasher vessel which divides the liquid product into a vapor phase and liquid phase which can be recycled to the reactor. It is the reactor-flasher combination and the interdependence between the liquid levels in the respective vessels, the interdependence of the reactor product flow rate and catalyst recycle flow rate and the interdependence between the liquid levels and the flow rates of the reactor product and recycle stream which renders control of the liquid levels in the reactor and flasher vessel difficult regardless of the particular reaction which is taking place in the reactor. The control system of the present invention can maintain the desired liquid levels without the constant oscillation of such levels and intermediate process stream flow rates to reduce process inefficiencies.

EXAMPLE

In this example, the level control system of the present invention was incorporated into a commercial reaction system for the carbonylation of methanol to acetic acid utilizing the low water process as previously described. The reaction process is that as described in FIG. 1 wherein water level in the reactor was maintained at between 3 to 5 wt. % of the liquid reaction medium. The level control system in place was that illustrated in FIG. 6. The level transmitters utilized to signal the actual liquid levels in the reactor and flasher vessels were electronic differential pressure transmitters. The transmitters include a sensing diaphragm sandwiched between liquid side and vapor side isolating diaphragms. The position of the sensing diaphragm which varies depending upon the respective pressures applied to the isolating diaphragms is measured by a variable capacitance which is amplified and converted to a milliampere current. The methanol feed flow transmitter was an orifice in which differential pressure across the orifice was transmitted by an electronic differential pressure transmitter as described above. The flow control valves for controlling the flow of reactor product from the reactor to the flasher and of catalyst recycle flow from the flasher to the reactor were rotary valves manufactured by Valtek Company. The controllers including the proportional controllers, function generators and summers as depicted in FIG. 6 were contained in the Honeywell TDC-3000 Distributed Control System which is a computer software system marketed by Honeywell Corporation.

Figure 7A:
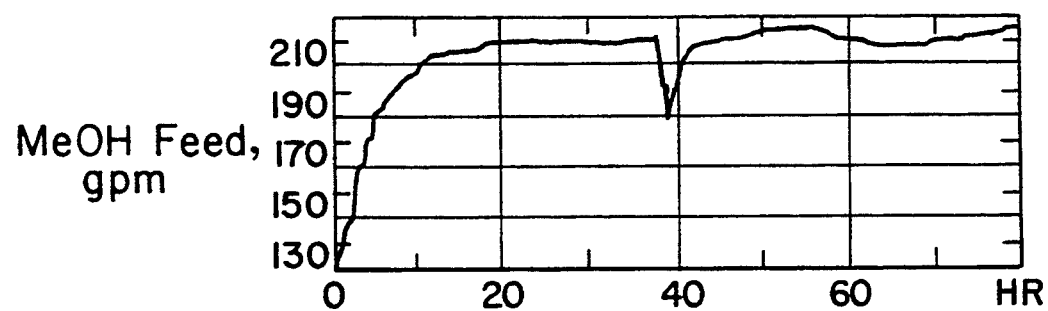
FIGS. 7(a)-(c) is a series of graphs which have been generated from the carbonylation of methanol to acetic acid under conditions and the control scheme of the present invention and which illustrate a side by side comparison of methanol feed rate and reactor product flow rate to the flasher and flasher recycle rate to the reactor.
Figure 7B:
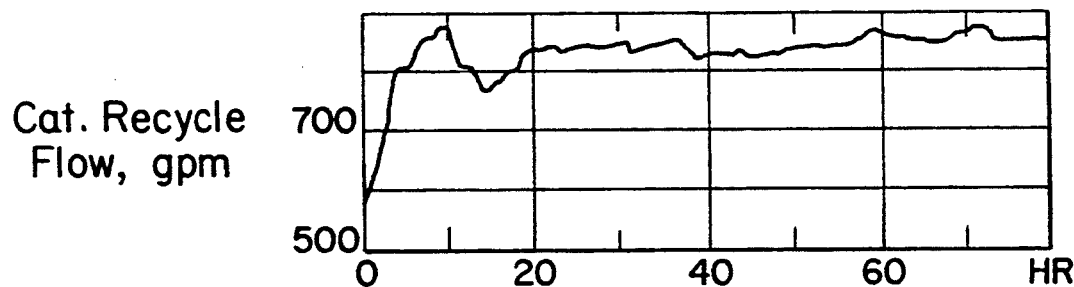
Figure 7C:
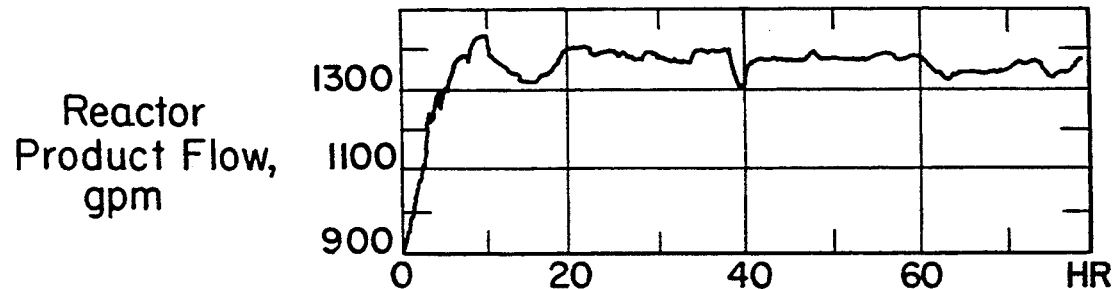

The control system was put in place for 80 hours. FIG. 7 illustrates a comparison between the methanol feed rate (FIG. 7a), catalyst recycle flow rate (FIG. 7b) and the reactor product flow rate (FIG. 7c) over the 80 hour span. From 0 to 15 hours, the methanol feed was continuously increased. From 15 to 80 hours, the methanol feed was substantially constant except for a sharp dip at around hour 40 which was necessitated in view of a unexpected drop in CO pressure. A comparison of the three Figures illustrates that the catalyst recycle flow and reactor product flow were relatively constant subsequent to the 15th hour.

What is claimed is:

1. In a reaction system for the carbonylation of methanol to acetic acid comprising:
   (a) a reactor containing a liquid reaction medium of methanol, a rhodium catalyst, a solvent and water to form a reactor product;
   (b) a flasher for receiving said reactor product from said reactor and capable of flashing off product acetic acid as vapor and forming a liquid at a base of said flasher containing rhodium;
   (c) means to direct said reactor product from said reactor to said flasher;
   (d) means to recycle said rhodium from the base of said flasher to said reactor;
   (e) means to feed methanol to said reactor;
   (f) means to control the liquid level in said reactor to a desired liquid level;
   (g) means to control the liquid level in said flasher to a desired liquid level;
   (h) means to control the flow rate of said reactor product from said reactor to said flasher;
   (i) means to control the flow rate of said recycled rhodium from said flasher base to said reactor;
   the improvement comprising:
   said reactor liquid level control means (f) containing;
   (j) means to determine the actual liquid level in said reactor and transmit a level signal;
   (k) controller means to receive said level signal, to determine any differences in liquid level between said desired liquid level in said reactor and said actual liquid level therein and to send a correction signal, said controller means being such as to not endlessly seek a zero off-set from said desired level;
   (l) means to determine the methanol feed rate in said methanol feed means (e) and to send a methanol feed rate signal;
   (m) a function generator means to receive said methanol feed rate signal and correlate said methanol feed rate to a desired reactor product flow rate from said reactor to said flasher by means of a first function which depicts the empirical relationship between said methanol feed rate and said reactor product flow rate from said reactor to said flasher under steady state conditions, and to convert said desired reactor product flow rate to a bias signal and to send said bias signal;
   (n) means to sum said correction signal and said bias signal to form a command signal and send said command signal;
   (o) a flow control means for receiving said command signal and for adjusting the flow rate of said reactor product in said means to control the flow rate of said recycled rhodium (h);
   said flasher liquid level control means (g) containing;
   (p) means to determine the actual liquid level in said flasher and transmit a flasher level signal;
   (q) controller means to receive said flasher level signal, to determine any differences between said desired liquid level in said flasher and said actual liquid level therein and to send a second correction signal, said controller means being such as to not endlessly seek a zero off-set from said desired liquid level in said flasher;
   (r) a function generator means to receive said methanol feed rate signal and correlate said methanol feed rate to a desired recycle flow rate from said flasher to said reactor by means of a second function which depicts the empirical relationship between said methanol feed rate and said recycle product flow rate from said flasher to said reactor under steady state conditions, and to convert said desired recycle flow rate to a second bias signal and to send said second bias signal;
   (s) means to sum said second correction signal and said second bias signal to form a second command signal and send said second command signal; and
   (t) a second flow control means for receiving said second command signal and for adjusting the flow rate of said recycle rhodium in said means (i).

2. The improved reaction system of claim 1 wherein said reaction medium contains less than 14 wt. % water.

3. The improved reaction system of claim 1 wherein said solvent is acetic acid.

4. The improved reaction system of claim 2 wherein said solvent is acetic acid.

5. The improved reaction system of claim 2 wherein said reaction medium further includes methyl acetate, an alkyl iodide and an additional iodide salt.

6. The improved reaction system of claim 5 wherein said iodide salt is lithium iodide.

7. The improved reaction system of claim 1 wherein said controller means (k) and (q) are proportional only controllers.

8. The improved reaction system of claim 1 wherein said controller means (k) and (q) are controllers with a lead-lag element.

9. The improved reaction system of claim 5 including means to treat said product acetic acid vapor from said flasher in a splitter column to form a product stream comprising acetic acid and water and a separate stream containing alkyl iodide and iodide salt.

10. The improved reaction system of claim 9 including means to distill said product stream from said splitter column to remove water from said acetic acid and form a dry acetic acid product.

11. In a reaction system comprising:
   (a) a reactor containing a liquid reaction medium to form a reactor product;
   (b) a flasher for receiving said reactor product from said reactor and capable of flashing off said product as vapor and forming a liquid bottoms at a base of said flasher;
   (c) means to direct said reactor product from said reactor to said flasher;
   (d) means to recycle said bottoms from the base of said flasher to said reactor;
   (e) means to feed reactant to said reactor;
   (f) means to control the liquid level in said reactor to a desired liquid level;
   (g) means to control the liquid level in said flasher to a desired liquid level;
   (h) means to control the flow rate of said reactor product from said reactor to said flasher;
   (i) means to control the flow rate of said recycled bottoms from said flasher base to said reactor;
   the improvement comprising:
   said reactor liquid level control means (f) containing;
   (j) means to determine the actual liquid level in said reactor and transmit a level signal;
   (k) controller means to receive said level signal, to determine any differences in liquid level between said desired liquid level in said reactor and said actual liquid level therein and to send a correction signal, said controller means being such as to not endlessly seek a zero off-set from said desired level;

(l) means to determine the feed rate of said reactant in said methanol feed means (e) and to send a reactant feed rate signal;

(m) a function generator means to receive said reactant feed rate signal and correlate said reactant feed rate to a desired reactor product flow rate from said reactor to said flasher by means of a first function which depicts the empirical relationship between said reactant feed rate and said reactor product flow rate from said reactor to said flasher under steady state conditions, and to convert said desired reactor product flow rate to a bias signal and to send said bias signal;

(n) means to sum said correction signal and said bias signal to form a command signal and send said command signal;

(o) a flow control means for receiving said command signal and for adjusting the flow rate of said reactor product in said means to control the flow rate of said reactor product (h);

said flasher liquid level control means (g) containing;

(p) means to determine the actual liquid level in said flasher and transmit a flasher level signal;

(q) controller means to receive said flasher level signal, to determine any differences between said desired liquid level in said flasher and said actual liquid level therein and to send a second correction signal, said controller means being such as to not endlessly seek a zero off-set from said desired liquid level in said flasher;

(r) a function generator means to receive said reactant feed rate signal and correlate said reactant feed rate to a desired recycle flow rate from said flasher to said reactor by means of a second function which depicts the empirical relationship between said reactant feed rate and said recycle product flow rate from said flasher to said reactor under steady state conditions, and to convert said desired recycle flow rate to a second bias signal and to send said second bias signal;

(s) means to sum said second correction signal and said second bias signal to form a second command signal and send said second command signal; and (t) a second flow control means for receiving said second command signal and for adjusting the flow rate of said recycle bottoms in said means (i).

12. The improved reaction system of claim 11 wherein said controller means (k) and (q) are proportional only controllers.

13. The improved reaction system of claim 11 wherein said controller means (k) and (q) are controllers with a lead-lag element.

14. The improved reaction system of claim 11 wherein said first and second functions are nonlinear.

15. The improved reaction system of claim 11 wherein said first and second functions are segmented linear approximations of a non-linear empirical relationship between said reactant feed rate and said respective reactor product flow rate and said recycle flow rate.

16. The improved reaction system of claim 11 wherein said means (f) and (g) to determine the actual liquid level in said reactor and said flasher comprises means to determine the differential pressure between said liquid and vapor in said vessels.

17. The improved reaction system of claim 11 wherein said means (l) to determine the reactant feed rate comprises an orifice and a means to determine the differential pressure of said reactant feed across said orifice.

18. The improved reaction system of claim 11 wherein means (h) and (i) are valves.

* * * * *